United States Patent [19]

Valet

[11] Patent Number: 4,751,188

[45] Date of Patent: Jun. 14, 1988

[54] METHOD FOR THE SIMULTANEOUS QUANTITATIVE DETERMINATION OF CELLS AND REAGENT THEREFOR

[75] Inventor: Günter Valet, Munich, Fed. Rep. of Germany

[73] Assignee: Max-Planck-Gesellschaft zur Foerderung der Wissenschaften e.V., Goettingen, Fed. Rep. of Germany

[21] Appl. No.: 541,562

[22] Filed: Oct. 13, 1983

[30] Foreign Application Priority Data

Oct. 15, 1982 [DE] Fed. Rep. of Germany ..... 32383533

[51] Int. Cl.⁴ .................... G01N 33/48; G01N 33/49
[52] U.S. Cl. .................... 436/63; 250/461.2; 356/39; 436/10; 436/800; 424/7.1
[58] Field of Search .............. 250/461.2; 356/39; 436/800, 10, 63; 424/7.1

[56] References Cited

U.S. PATENT DOCUMENTS

| | | |
|---|---|---|
| 3,560,754 | 2/1971 | Kamentsky ............... 356/39 |
| 3,657,537 | 4/1972 | Wheeless et al. ............... 356/39 |
| 3,675,768 | 7/1972 | Legorreta-Sanchez ............... 356/39 |
| 3,684,377 | 8/1972 | Adams et al. ............... 356/39 |
| 3,710,933 | 1/1973 | Fulwyler et al. ............... 356/39 |
| 3,770,349 | 11/1973 | Legorreta-Sanchez ......... 250/461.2 |
| 3,824,402 | 7/1974 | Mullaney et al. ............... 356/39 |
| 4,284,355 | 8/1981 | Hansen et al. ............... 356/39 |
| 4,284,412 | 8/1981 | Hansen et al. ............... 436/548 |
| 4,299,726 | 11/1981 | Crews et al. ............... 435/4 |
| 4,338,024 | 7/1982 | Bolz et al. ............... 356/39 |
| 4,400,370 | 8/1983 | Kass ............... 424/7.1 |
| 4,559,309 | 12/1985 | Evenson et al. ............... 436/172 |
| 4,584,277 | 4/1986 | Ullman ............... 436/800 |

*Primary Examiner*—Sam Rosen
*Attorney, Agent, or Firm*—Felfe & Lynch

[57] ABSTRACT

For the simultaneous quantitative determination of the blood cells or other cells, the cell blood sample is incubated with a fluorescent stain cocktail containing fluorescent dyes and calibration particles and which stains at least one characteristic of the blood cells, and then the volume and the fluorescence of the cells and particles are measured simultaneously at at least one wavelength.

9 Claims, 15 Drawing Sheets

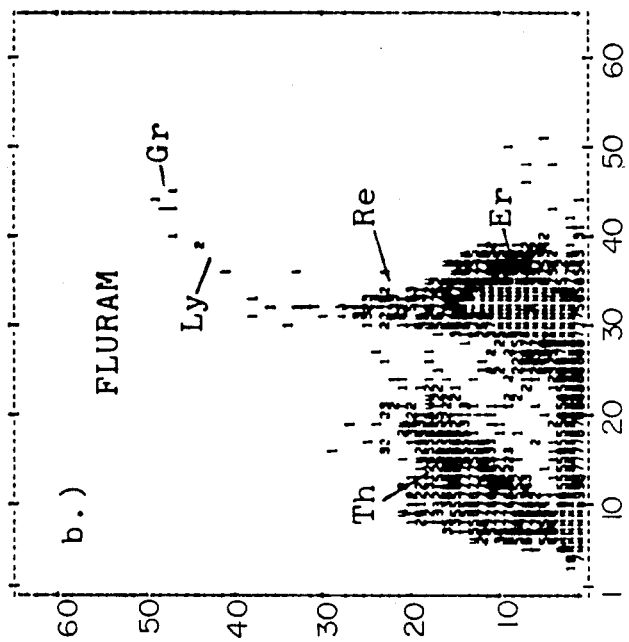
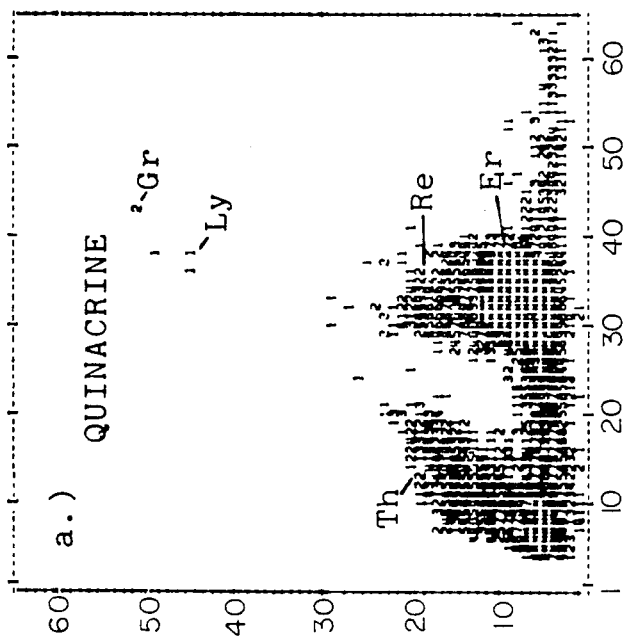
FIG. 3a
FIG. 3b

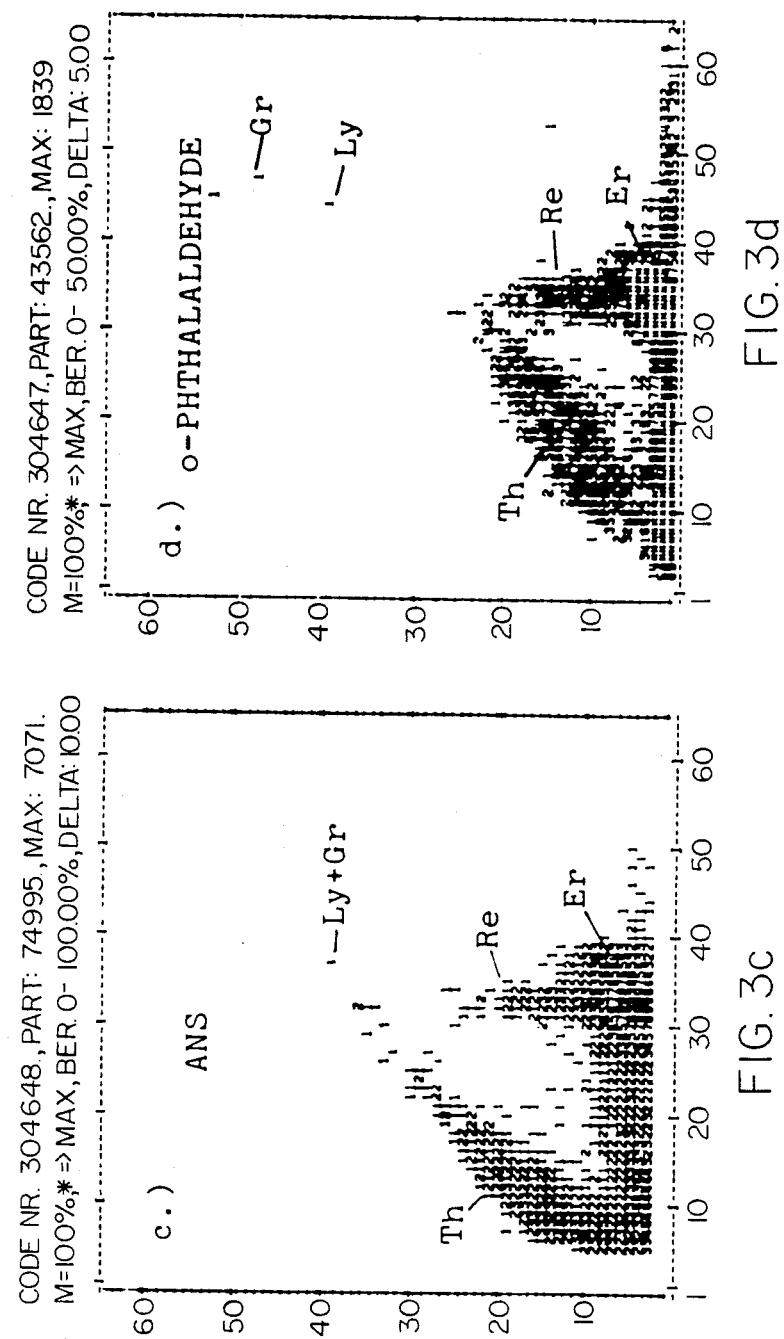

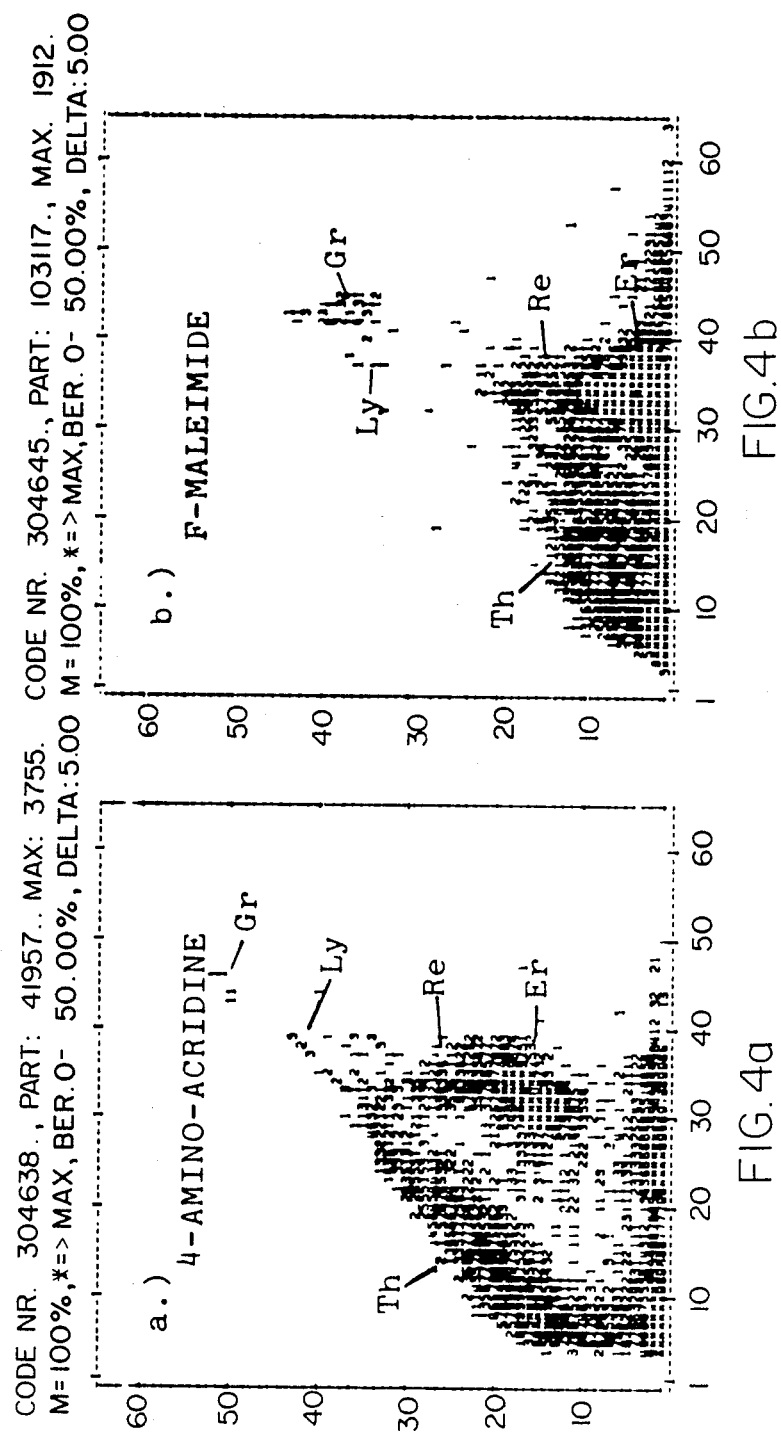

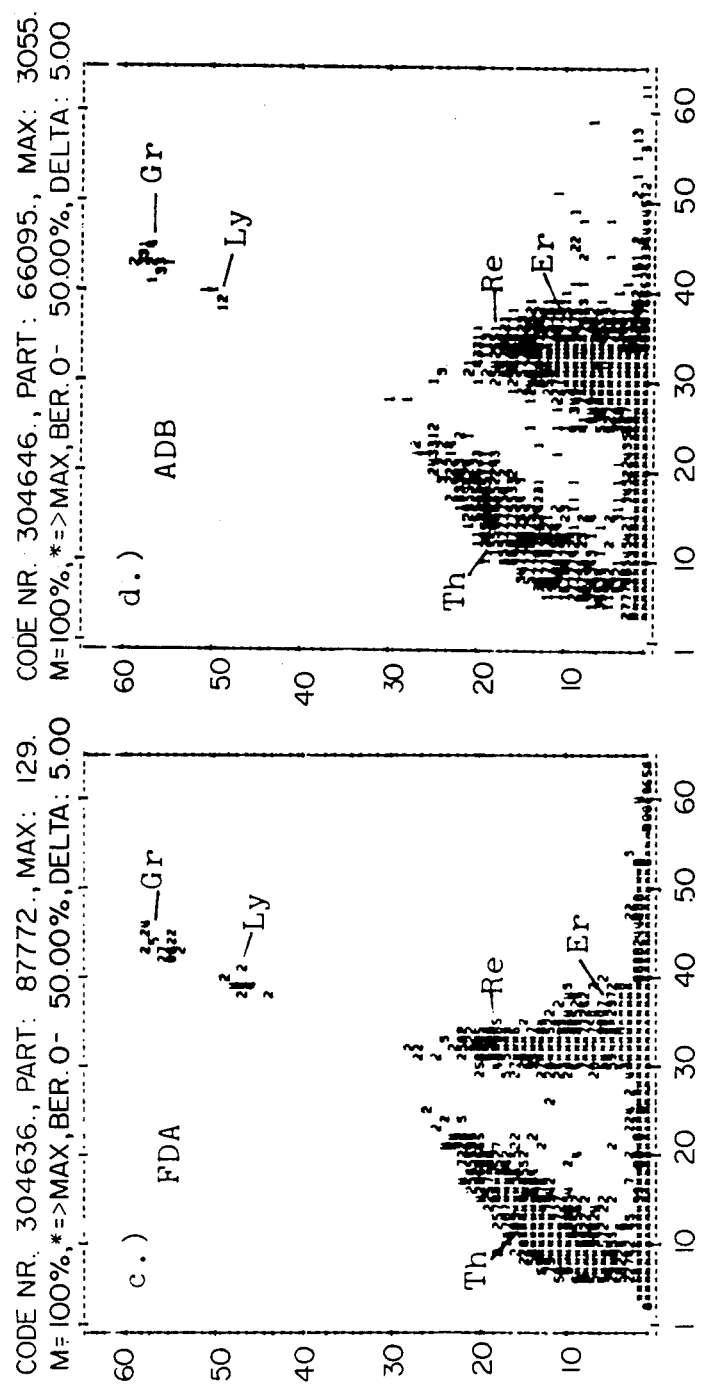

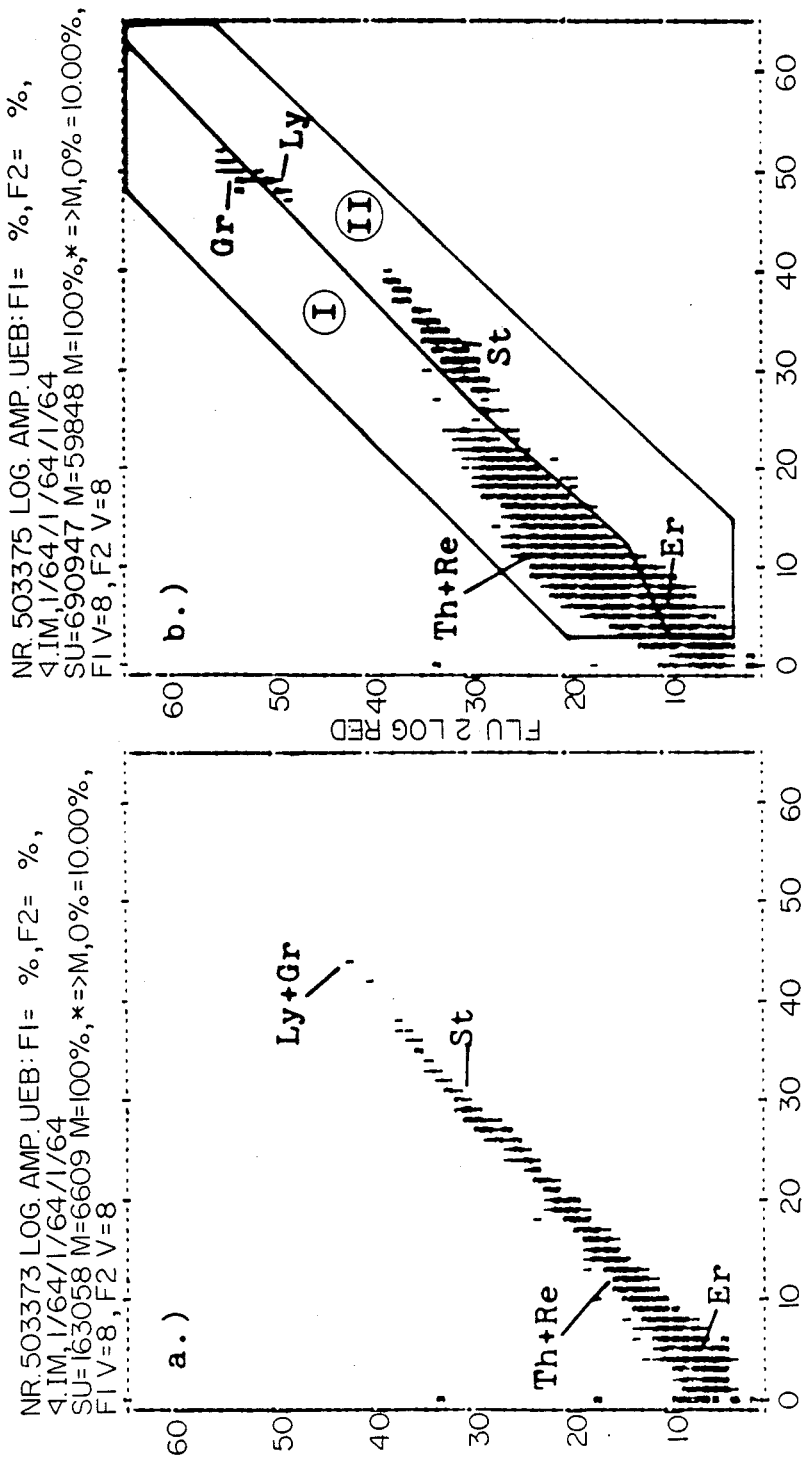

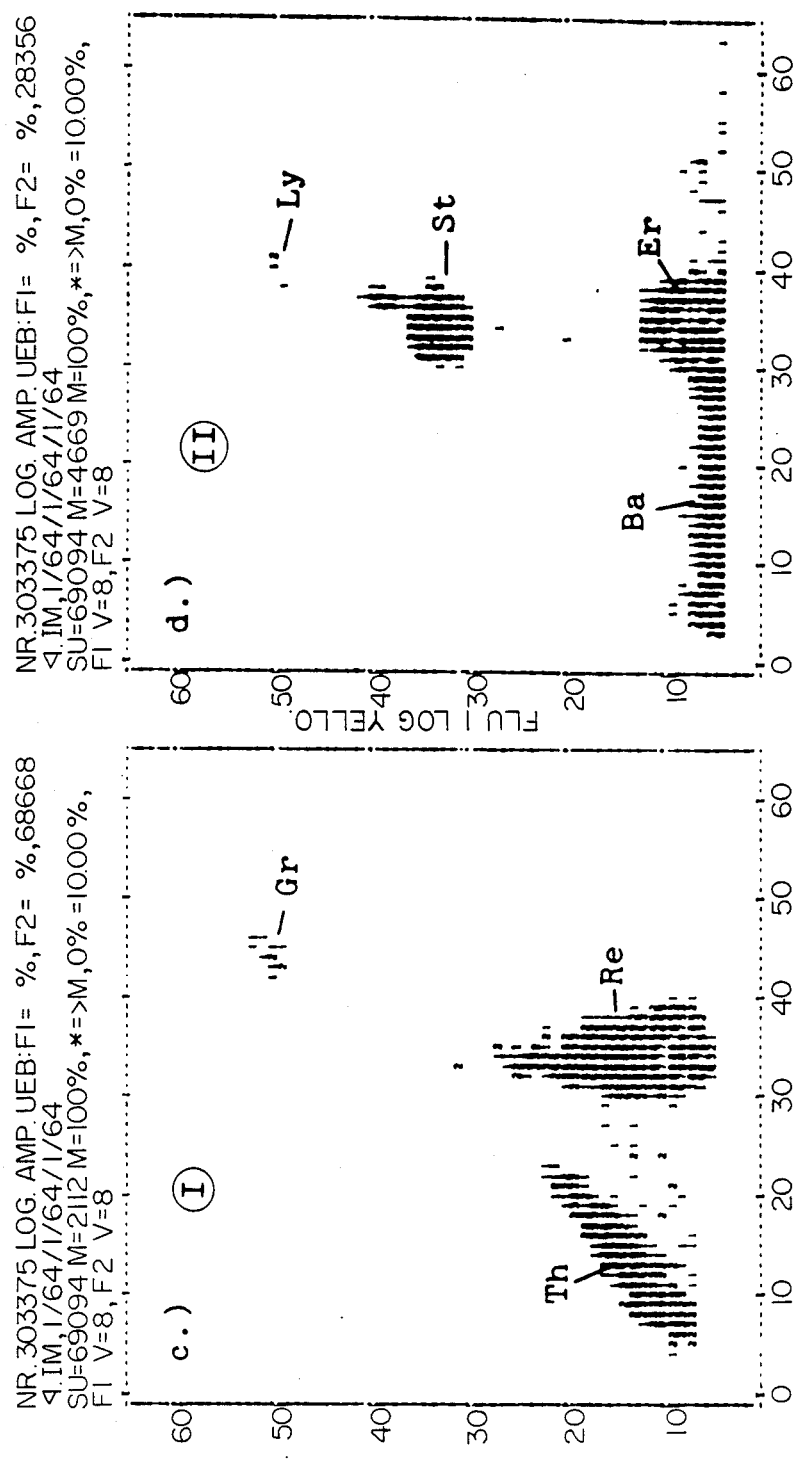

METHOD FOR THE SIMULTANEOUS QUANTITATIVE DETERMINATION OF CELLS AND REAGENT THEREFOR

DESCRIPTION

The invention relates to a method for the simultaneous quantitative determination of cells and to a reagent suitable for the practice thereof.

The blood cell count is one of the most frequently ordered laboratory tests in hospital and general medical practice. It is estimated that in the Federal Republic of Germany alone, ten thousand such tests are performed daily. The test is of particular importance in the treatment of accident victims, intensive care medicine, and in the operating room.

To obtain a complete blood count, usually six separate tests are performed on each blood sample:

1. Erythrocyte count (electrical counters, counting chambers)
2. Leucocyte count (electrical counters, counting chambers)
3. Thrombocyte count (electrical or scattered light counters, counting chambers)
4. Hematocrit (centrifuge) for computing the average erythrocyte volume (MCV)
5. Reticulocytes (staining with brilliant cresyl blue, smearing and counting)
6. Leucocyte differentiation (smearing, May-Gruenwald-Giemsa staining, and counting.)

Particularly reticulocyte and thrombocyte counting and the differential blood count are time-consuming or difficult methodologically. For example, the time required for a quantitative determination of the blood cells is measured in hours. The same also applies to the determination of other cells in the form of single cells, for example by mechanical or chemical disintegration of tissue. Therefore there is a need for the development of more rapid and automatable methods which will permit a substantial reduction of the great amount of time and person-hours heretofore required This problem is solved in accordance with the invention by a method for the simultaneous quantitative determination of cells, which is characterized by the fact that the sample containing the cells that are to be counted is stained with a fluorescent dye which stains at least one property of the blood cells, and then measuring simultaneously the volume and the fluorescence of the cells at at least one wavelength.

The method of the invention is based on the principle that characteristics of the cells are stained by dyes and are measured simultaneously with the cell volume, for example in a flow-through cytometer. Through the simultaneous determination of the volume and fluorescence of the stained cells, which is performed in an automatic apparatus, each individual cell is tested qualitatively and quantitatively, and can be classed as a certain blood cell on the basis of the determined cell volume and fluorescence, since each type of cell is characterized by specific values of fluorescence and cell volume. In this manner it is possible, for example, to produce a complete blood count within a few minutes, with a minimum occupation of personnel.

The cell characteristics which are indicated by the stains used in accordance with the invention, are characteristics of state or characteristics of function. State characteristics are those which are produced by cellular synthesis, such as, for example, DNS, RNS, proteins and lipids, while functional characteristics are those which result from metabolical processes, such as, for example, transmembrane potential and intracellular pH.

Particularly well-suited for the method of the invention is the simultaneous staining of the cells with a DNA/RNA stain and a membrane-potential-sensitive stain, and therefore this is preferred. DNA/RNA stains which are especially suited for this preferred embodiment of the invention are acridine orange (AO), quinacrine and pyronine Y, the first being especially preferred. Of the group of the membrane-potential-sensitive stains, 3,3'-dihexyl-oxa-carboxyanine [sic] (DiOC6(3)) is preferred. The preferred substances are excitable in the same spectral range by the same light source, and therefore they are suitable for the preparation of a premixed reagent which can be added to the cell samples.

Examples of other stains from the above-mentioned group that are suitable in the scope of the invention are: fluorescamine (Fluram), (1-anilinonaphthalin-8-sulfonic acid (ANS) and o-phthalaldehyde for the staining of the cell protein, 4-aminoacridine for staining the lipids, N-(3-fluoanthyl)maleimide for staining free SH groups, fluoresceindiacetate (FDA) for staining enzyme activities (in the cited case of ester activity) and 1,4-diacetoxy-2,3-dicyano-benzene (ADB) for staining the intracellular pH.

The volume and the size spectrum of the cells are determined either by light scattering (J. Histochem. Cytochem. 27, 359-365 (1979)) or by measurement of the change in electrical resistance during passage through a narrow opening (Coulter's method, cf., e.g., "Flow cytometry and sorting," by Melamed, Mullaney and Mendelsohn, John Wiley and Sons, Inc. 1979, pages 61 to 101). Coulter's method is preferred. It is based on letting the blood sample run through a short orifice of small diameter and measuring at this point the change in the electrical resistance, the particle resistance differing from that of the electrolyte. The voltage change which takes place upon the passage of a cell through the orifice across which a constant electric current is applied between two electrodes, is directly proportional to the particle volume.

Incubation with the stain can be performed conveniently in a few minutes at room temperature. Generally, 1 to 10 minutes, preferably 2 to 6 minutes, of standing at room temperature will suffice, counting from the addition of a solution of the stains to the blood sample being tested, which it is desirable to dilute appropriately beforehand with isotonic sodium chloride solution. After the incubation, the sample to be tested is placed in a suitable apparatus, for example a commercially available flow-through cytometer, which must be set up such that the cell volume and the fluorescence can be determined simultaneously and thus the volume measured for each particle can be associated with a corresponding fluorescence measurement.

The electrical method is preferred, since the experimentally determined stain contents of the individual cells of each type can be expressed as stain concentrations, since absolute volumes are measured. Thus, the measured properties of the cell types can be compared directly with one another in a standardized manner. In the light-scattering method, however, this is not possible, since the light scattering depends not only on the cell volume and shape but also on the nature of the cell surface and cell interior.

In the preferred embodiment of the invention using acridine orange (AO) in combination with DiOC6, use is made of the fact that all blood cells except the erythrocytes are well stained by AO, while the erythrocytes are also well stained by DiOC6 but at the same time the staining of the other cells is improved.

In another preferred embodiment of the invention, the measurement is performed in the presence of a fluorescent monodisperse calibration phase, especially one stained with a fluorescent dye. If the fluorescent calibration phase that is added is in a known concentration, it is possible to determine the absolute concentrations of the different cells in the blood. A preferred calibration phase is monodisperse latex particles having a diameter of 1 to 10 microns, and those of a diameter between 4 and 6 microns are especially preferred. However, other fluorescent particles of known uniform size in the blood cell range and of known concentration can be used.

The practice of the method of the invention is extremely simple. Blood is treated with physiological sodium chloride solution and the stain, plus the particles of the calibration phase, if used. After, for example, three to five minutes of staining time, the stained blood cells are measured in a suitable apparatus, using, for example, a commercially available flow-through cytometer, at a rate of about 2000 cells per second over a period of about 5 to 15 minutes. In this manner all types of blood cells in sufficient amount can be determined quantitatively.

If tissue cells are to be determined, they are first set free by the disintegration of the tissue, e.g., by cutting it up with a "tissue chopper." The rest of the procedure is then the same as that described above for blood cells.

The method of the invention furthermore makes it possible to measure not one but several fluorescences separately. In the preferred embodiment of the method, using AO and DiOC6, for example, both the yellow fluorescence of native DNA/RNA (spiralized form) and the red fluorescence of the despiralized form can be determined. In this manner it becomes possible also to learn something about the functional state of the blood cells. The method of the invention therefore makes it possible, in this embodiment, not only to perform a quantitative blood count, but also to say something about the functional state of the individual types of cells determined, and this is not possible by known methods.

The stains used in accordance with the invention can be determined not only with optical systems equipped with mercury or xenon lamps, but also with those provided with lasers.

Additional subject matter of the invention is a reagent for the practice of the method of the invention. This reagent is characterized by the fact that it contains a fluorescent stain from the group: DNA/RNA stains, cell protein stains, lipid stains, enzyme stains, membrane-potential-sensitive stains, intracellular pH stains, SH-group stains, and, additionally, a monodisperse calibration phase.

A preferred reagent of the invention contains a DNA/RNA stain and a membrane-potential-sensitive stain.

Especially preferred is a reagent which contains acridine orange, 3,3'-dihexyl-oxy-carbocyanine, monodisperse latex particles of 1 to 10 microns diameter, and a solvent.

Suitable solvents for the reagent of the invention are those which can dissolve in sufficient concentration the stain selected in each case and the monodisperse phase, without attacking the particles of the calibration phase, for example by starting to dissolve them. Preferred solvents are dimethylsulfoxide, dimethylformamide and alkanols.

The invention brings it about that all types of cells can be determined quantitatively and simultaneously in a few minutes, the rapid staining and the complete automatability of the procedure, namely the staining, the measurement and the evaluation, playing a decisive role. In addition, it is possible also to obtain indications of the functional state of the individual kinds of cells.

Furthermore, the method makes possible not only a reduction of the time required for measurements and an improvement of the information obtainable therefrom, but also it can be applied over an especially large range of measurement, amounting to approximately 2.5 decades log, i.e., approximately 1:500.

The importance of this advantage can be seen from the following: If one sets out from the normal concentrations of the different blood cells, which in the case of erythrocytes is around $5 \times 10^6$, in that of thrombocytes about $3 \times 10^5$, and in the case of leucocytes about $5 \times 10^3$ per mm$^3$, it can be seen that a broader range of measurement is essential if all these blood cells are to be determined simultaneously. Thus it has been difficult heretofore to determine thrombocyte concentrations under 5 to $7 \times 10^5$ per mm$^3$. By the invention, this bottom limit has been reduced to $1 \times 10^3$ per mm$^3$. This is important because it is precisely in the range of 100,000 and 30,000 per mm$^3$ that the especially critical ranges lie. In the former case this is the pathological range, and in the latter case the acutely dangerous range.

Another possibility for the application of the method of the invention consists in the study of the effect of medication on individual cells, as for example the action of cytostatic medication on tumor cells. Especially in the case of medication of high toxicity, this permits preliminary testing as to whether their effectiveness in the special individual justifies the acceptance of the toxic side-effects or not. For example, individual cells can be obtained mechanically from tumor tissue, tested in a suitable nutrient medium, such as heparinized patient blood plasma, in the presence of the medication being tested, and then it will be possible to determine quantitatively, by the method of the invention, what percentage of the tumor cells have been killed by the medication and what percentage survive. The method of the invention can thus be used to determine the most effective medication of several medications under consideration.

The following examples, in conjunction with the drawing, will further explain the invention. In the drawing, FIG. 1 is a diagrammatic representation of a flow-through cytometer suitable for the practice of the invention, FIG. 2 is a graphic representation of cell volume versus fluorescence of a stained (a) and an unstained (b) blood sample diluted 1:250 (Th=thrombocytes, Er-=erythrocytes, Re=reticulocytes, St=calibration particles, Ly=lymphocytes, Gr=granulocytes, Ba=base line), FIG. 3 is a graphic representation like that of FIG. 2, using different stains, 3a is Quinacrine; 3b is Fluram, 3c is ANS; 3d is o-phthaladehyde.

EXAMPLE 1

Figure 1:
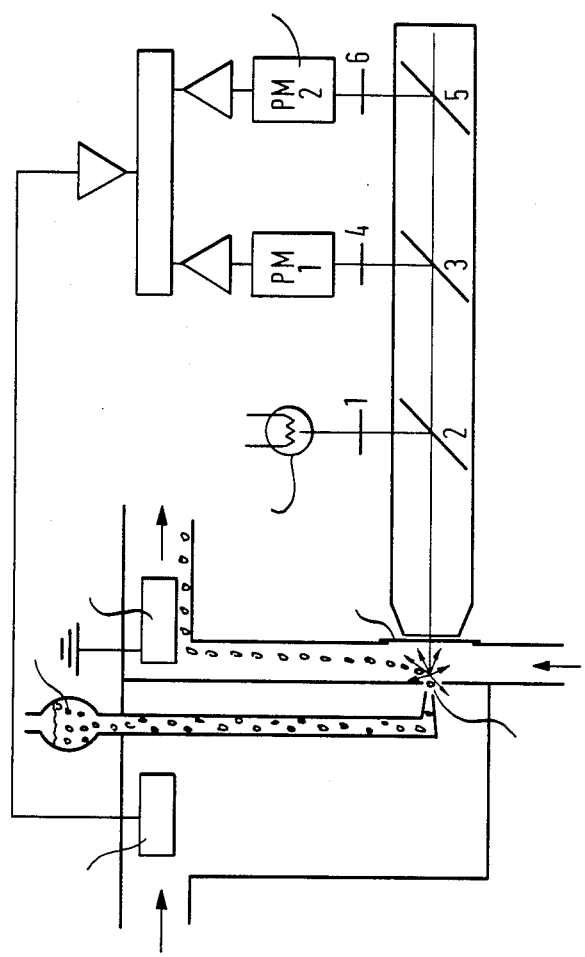

5 microliters of blood are taken from the fingerpad and diluted 1:250 with isotonic sodium chloride solution (0.15 M NaCl with 10 mM TRIS/HCL pH 7.4, (TBS)). 500 microliters of the cell suspension are incubated with 5 microliters of reagent (AO 0.4 mg/ml, DiOC6 0.02 microgram per ml and 4-micron, monodisperse latex particles stained with FITC of a concentration of $5 \times 10^7$ per ml) for 3 to 5 minutes at room temperature. Dimethylsulfoxide (DMSO) is used as the solvent and suspension medium for the reagent. The suspension is thoroughly mixed by shaking and placed for measurement in a flow-through cytometer whose principle of construction is represented in FIG. 1 of the appended drawing. This apparatus is commercially obtainable under the name Fluvo-Metricell. In the case of staining with AO/DiOC6, the following filters and mirrors are used:

1—short-pass (KP) 500 nm with long-pass (LP) 418 nm filter;
2—dichroic splitter mirror (D) 500 nm;
3—reflective mirror for two-parameter measurement or D 530 nm for three-parameter measurement;
4—LP 500 nm;
5—reflective mirror;
6—LP 550 nm.

AO/DiOC6 are excited between 418 and 500 nm. The fluorescent light emitted is collected in two-parameter measurements (volume against fluorescence 1) between 500 and 700 nm by the phototube 1 (PM1). In three-parameter measurements the yellow light is measured between 500 and 530 nm and the red light between 550 and 700 nm by PM1 and PM2.

For the results represented in FIGS. 2 to 6 of the drawing, the operations were performed with a cylindrical measurement orifice of 50 microns diameter and 50 microns length. The liquid system of the flow-through cytometer was filled with TBS buffer 25° C. The cell volume was measured at an electric current of 0.385 mA.

The fluorescence was excited by an HBO-100 high-pressure mercury lamp. The logarithmically amplified fluorescence and volume signals of the cells were either stored in a multichannel analyzer as two-parameter histograms, or recorded online on magnetic tape. The curves were plotted graphically and by computer. If a microprocessor-controlled data module is used, both the addition of stain and the measurement as well as the plotting can be made completely automatic.

Figure 2:
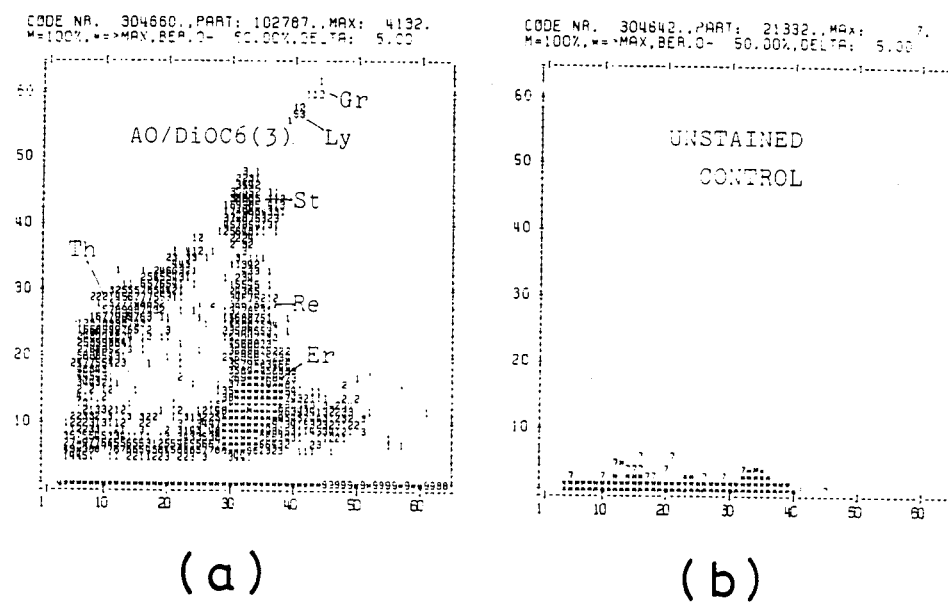
Figure 2A:
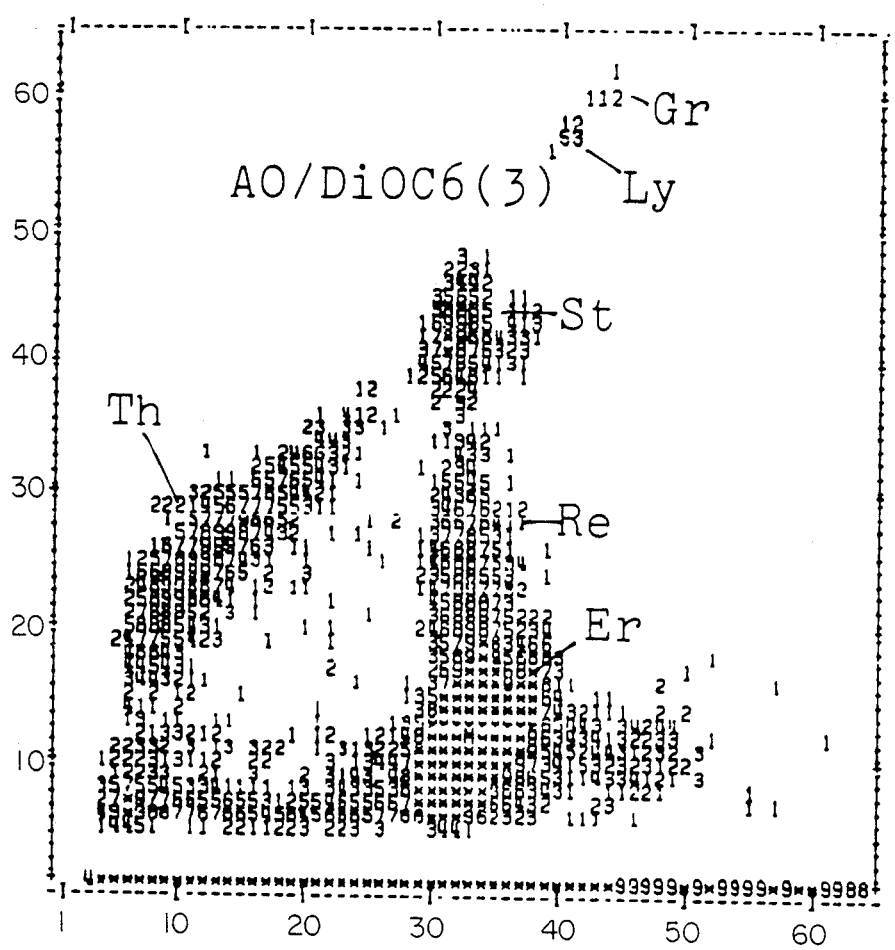
Figure 2B:
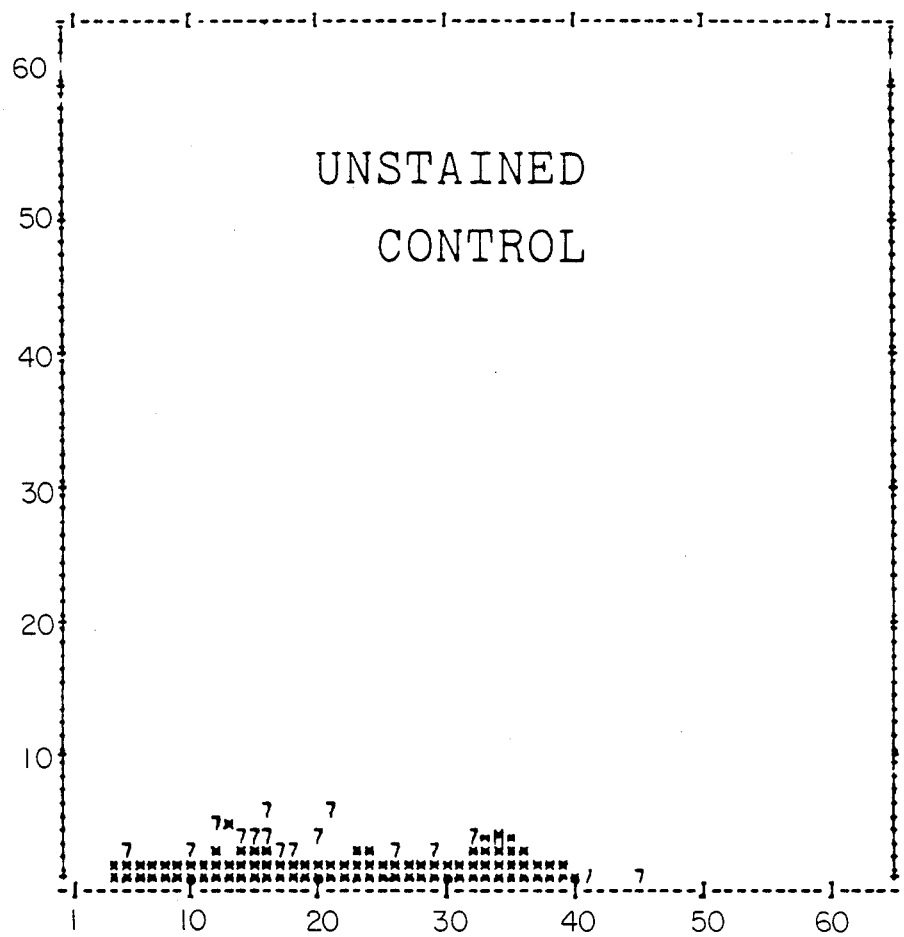

FIG. 2a is a graphic representation of cell volume versus fluorescence.

The computation by integration of the cell masses in FIG. 2a yields the following values:

|  | Thrombo-cytes | Erythro-cytes | Reticulo-cytes | Calibration particles | Lympho-cytes | Granulocytes |
| --- | --- | --- | --- | --- | --- | --- |
| Percentage | 4.60 | 91.62 | 1.62 | 2.02 | .024 | .045% |
| Conc. in the sample | 11.38 | 226.7 | 4.18 | 5.00 | .0594 | .111 × 10/ml |
| Conc. in the blood | 284500 | 5.66 × 10 | 104500 | — | 1485 | 2750 cells/ml |

FIG. 2 shows the result of a similar measurement without the addition of stain. No cell-bound fluorescence is observable.

The volume and fluorescence pulses of the FLUVO-METRICELL flow-through cytometer were logarithmated with the aid of 2.5 decades of logarithmic amplifiers, and then counted into the 64×64 matrix of a multichannel analyzer according to their maximum amplitude. For graphic representation, the channel contents of the matrix were logarithmated (3-decade amplitude log) and standardized on the value indicated at M. The maximum channel content (M) was divided into 20 equal parts (5% steps). Each channel content received a number between 1 and 10 corresponding to its relative frequency. Channel contents whose amplitude was higher than 50% of the maximum level were marked with an asterisk (*).

EXAMPLES 2 to 9

As described in Example 1, and using the same apparatus, simultaneous quantitative blood cell determinations were performed on 500 microliters of human blood, each sample diluted 1:250 and stained with 5 microliters of reagent in accordance with the following table:

| Example | Stain | Composition | Figure |
| --- | --- | --- | --- |
| 2 | Quinacrine | 0.2 mg/ml DMSO | 3a |
| 3 | Fluram | 1.0 mg/ml DMSO | 3b |
| 4 | ANS | 2.0 mg/ml DMSO | 3c |
| 5 | o-phthaldehyde | 3.0 mg/ml DMSO | 3d |
| 6 | 4-aminoacridine | 1.0 mg/ml ethanol | 4a |
| 7 | F—maleimide | 1.0 mg/ml DMSO | 4b |
| 8 | FDA | 0.04 mg/ml dimethylformamide | 4c |
| 9 | ADB | 1.0 mg/ml dimethylformamide | 4d |

Figure 3:
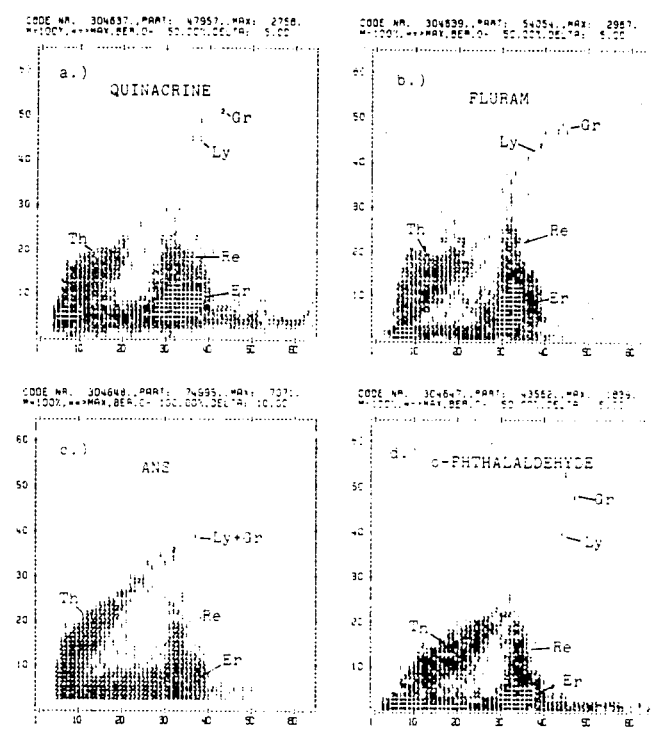
Figure 4:
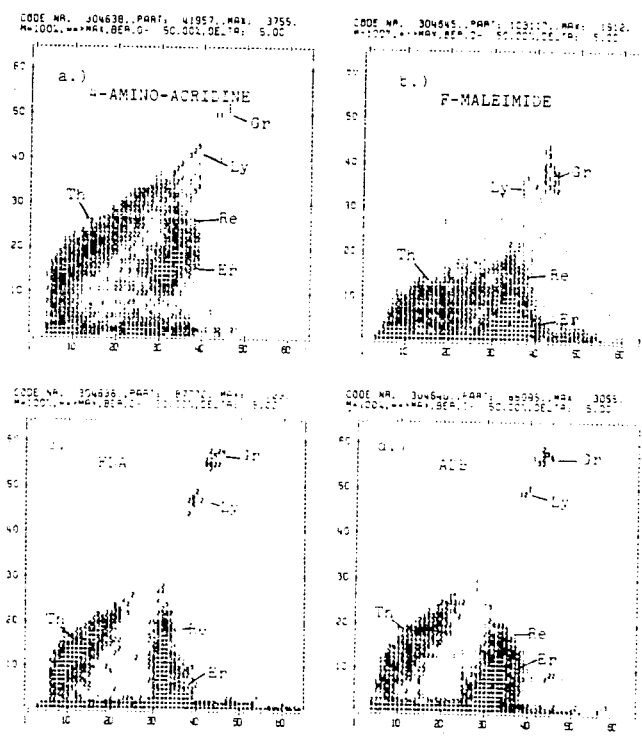
FIG. 4 is a graphic representation similar to FIG. 2, again using different stains.

The results are represented graphically in FIGS. 3 and 4.

EXAMPLE 10

In the manner described in example 1, a determination was performed with a blood sample stained with AO/DiOC6, but recording two different fluorescences, namely the yellow (fluorescence 1; transmembrane potential on the AO/DiOC6 staining) and the red (fluorescence 2; despiralized RNA/DNA. The analysis of these three parameters permits the measured data to be represented in the "cloud" form in FIG. 5.

Figure 5:
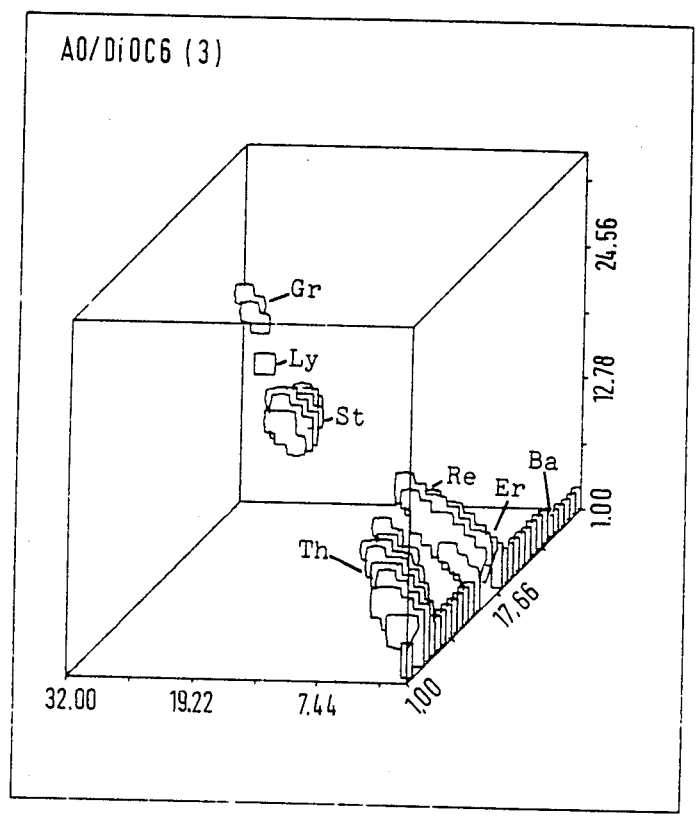
FIG. 5 is a graphic representation showing simultaneously three parameters, two fluorescences being recorded, plus the cell volume.
Figure 6:
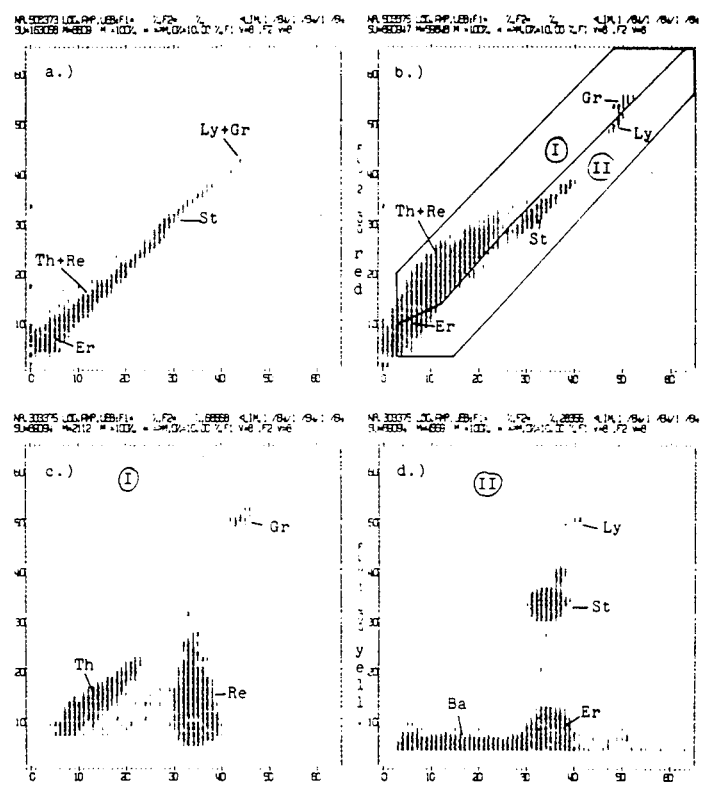
FIG. 6 is a graphic plotting of the two fluorescence measurements obtained in the three-parameter measurement of FIG. 5, so that the metabolic states of the cells can be determined therefrom.

Each scale in FIGS. 5 and 6 covers 2.5 logarithmic decades. The three measuring pulses for each individual cell were logarithmated for the representation in FIG. 5 and recorded ON-LINE on magnetic tape. For evaluation, the values were classes in a $32 \times 32 \times 342$ matrix and represented by means of a cloud program (Cytometry 1, 222–228 (1980)). The presence of cells and calibration particles is represented by a contour line at 1% of the maximum channel content. The individual types of cell and the calibration particle are easily distinguished from one another.

FIG. 6 gives a representation of the yellow fluorescence (Fluor. 1) against the red (Fluor. 2) for 3 parameter measurements in which human blood diluted 1:500 had been stained with DiOC6 (a) and with AO and DiOC6 simultaneously (b). As it can be seen, the three-parameter measurement makes it possible to determine the RNA content and RNA concentration of the different cell types. The additional AO staining gives the portion of curve 6b marked Th+Re a decided red shift. If the cell volume vs. fluorescence 1 histograms of the red-shifted (I) and unchanged (II) particles are drawn (c and d), comparison with FIG. 1a shows that the red cells containing RNA correspond to the thrombocytes (Th), the reticulocytes (Re) and the granulocytes (Gr), while the erythrocytes (Er), the calibration particles (St) and the lymphocytes (Ly) contain no RNA and therefore they retain their yellow fluorescence. The double staining also shows, as a by-product, that the reticulocytes have a higher membrane potential than the erythrocytes. This can be seen from FIGS. 6a and 6b. The cells lying directly over the erythrocyte cluster correspond to the zone identified in FIG. 6a as Th+Re. This zone is totally shifted into the red by the additional AO stain (6b), which means that the cells stained yellow by DiOC6 contain RNA. In the volume/fluorescence histogram, these cells correspond to the thrombocytes and reticulocytes. This shows that the DiOC6 stained cells lying above the erythrocytes are reticulocytes.

EXAMPLE 11

Fresh, sterile material from a lymph node metastasis of a mammary carcinoma is mechanically cut up with a tissue chopper, and the pieces are strained through a sieve having a mesh opening of 60 microns. The cells obtained are cultured for seven days in heparinized patient blood plasma as culture medium in microtitration dishes in the presence or absence of different cytostatic agents. Then the cell suspension is washed and stained for five minutes with 1,4-diacetoxy-2,3-dicyanobenzene (ADB) and propidium iodide (PI). ADB demonstrates the activity of the cytoplasma esterase and the intracellular pH of the living cells, and PI stains the DNA dead cells. The cell volume and the blue and the green fluorescence of the stained cells are measured simultaneously in a flow-through cytometer, as described in Example 1. Before the measurement, fluorescent monodisperse latex particles of 6 microns are added to the cell suspension as concentration and fluorescence standards. Cell volume, and the fluorescence signals of each cell which correspond to the pH, esterase activity and DNS, are measured simultaneously.

Figure 7:
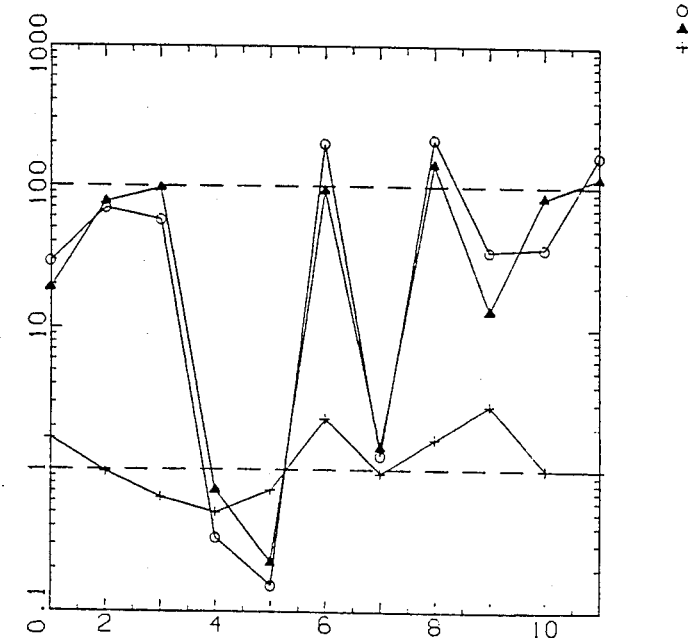
FIG. 7 is a graphic representation of the results of the testing of medication in cells of disintegrated lymph node metastases of a mammary carcinoma, in which the nature of the medication is plotted against the number of tumor cells in the one case and inflamed cells in the other.

The number of the tumor cells living in a culture of the surviving inflammation cells is then computed from their ratio to the number of standardized calibration particles. The results of the different cytostatic agents tested and of the untreated controls are combined in the resistance diagram shown in FIG. 7. The abscissa axis of the diagram identifies the individual medications and the controls, and the number of the tumor cells and inflammation cells in each case, with respect to 100% of the controls, is recorded on the ordinate axis. It can be seen that, in the case of cytostatic agents Nos. 1, 4, 5 and 7, a reduction of the tumor cells was achieved, while the other agents produced no effect. The effect on inflammation cells, which is a better indication of the less toxic agents, is determined separately. The ratio of remaining inflammation cells to tumor cells after the incubation is represented in the figure also as a therapeutic index.

I claim:

1. A method for simultaneously measuring the volume and at least one additional characteristic of cells in a specimen comprising the steps of adding, a predetermined amount of a staining reagent which simultaneously contains a fluroescent RNA/DNA stain, a fluoresecent membrane-potential-sensitive stain, fluorescing monodisperse calibration particles and an organic solvent in which said dyes dissolve, characterized in that said solvent does not attack said monodisperse particles, to a sample of the specimen to form a measurable mixture; incubating the specimen sample with the staining reagent and simultaneously measuring the volume and the fluorescence of the cells, the volume being determined by comparing a volume value obtained for said measurable mixture to a calibration standard volume value obtained for an amount of monodisperse particles equal to the monodisperse particles in said measurable mixture.

2. The method of claim 1, wherein at least one additional stain is used selected from the group consisting of, cell protein stains, lipid stains, enzyme stains, intracellular pH stains, and SH group stains.

3. The method of claim 2 wherein the DNA/RNA stain is acridine orange, quinacrine, or pyronine Y.

4. The method of claim 1 wherein 3,3-dehexyl-oxa-carbocyanine is used as the membrane-sensitive stain.

5. The method of claim 1, wherein the monodisperse calibration particles are monodisperse latex particles of 1 to 10 microns diameter.

6. The method of claim 1 wherein the measuring of the cell fluorescence comprises flowing the specimen sample through a narrow cross section conduit, irradiating the specimen sample as it is caused to flow through the conduit, with pulsed monochromatic light, laser light, or a mercury or zenon lamp to cause it to fluroesce, and measuring the fluorescence signals produced.

7. The method of claim 6 wherein the measuring of the cell volume comprises flowing the specimen sample through a narrow cross section conduit, and measuring the change in the electrical conductivity of the speciment sample as it flows through the conduit.

8. The method of claim 6 wherein the measuring of the cell volume comprises flowing the specimen sample through a narrow cross section conduit, and measuring the light scatter of the specimen sample as it flows through the conduit.

9. The method of claim 1 wherein the measurement is performed in a flow through cytometer.

* * * * *